United States Patent [19]

Wallace et al.

[11] Patent Number: 4,803,075
[45] Date of Patent: Feb. 7, 1989

[54] INJECTABLE IMPLANT COMPOSITION HAVING IMPROVED INTRUDABILITY

[75] Inventors: Donald G. Wallace, Menlo Park; Hertsel Reihanian, San Francisco; Bruce B. Pharriss, Palo Alto; William G. Braun, Los Altos, all of Calif.

[73] Assignee: Collagen Corporation, Palo Alto, Calif.

[21] Appl. No.: 878,418

[22] Filed: Jun. 25, 1986

[51] Int. Cl.⁴ .................................................. A61F 2/00
[52] U.S. Cl. ...................................... 424/423; 424/400; 514/18; 514/801; 514/802
[58] Field of Search ............... 424/423, 499, 500, 501, 424/400; 514/18, 801, 802

[56] References Cited

U.S. PATENT DOCUMENTS

| 3,949,073 | 4/1976 | Daniels et al. ................ 424/177 |
| 4,107,288 | 8/1978 | Oppenheim et al. ............. 424/499 |
| 4,233,360 | 11/1980 | Luck et al. ................ 514/801 X |
| 4,424,208 | 6/1984 | Wallace et al. ............... 424/177 |
| 4,440,750 | 4/1984 | Glowacki et al. ............... 424/95 |
| 4,442,655 | 4/1984 | Stroethmann .............. 424/423 X |
| 4,582,640 | 5/1986 | Smestad et al. ............. 260/123.7 |
| 4,617,293 | 10/1986 | Wahlig et al. ................. 514/37 |

FOREIGN PATENT DOCUMENTS

0264621 6/1970 U.S.S.R. ........................... 514/801

Primary Examiner—Thurman K. Page
Attorney, Agent, or Firm—Ciotti & Murashige, Irell & Manella

[57] ABSTRACT

Injectable aqueous suspensions of biomaterials, such as cross-linked collagen, that contain a biocompatible fluid lubricant, such as glycogen or maltose, are disclosed. The inclusion of the lubricant significantly improves the intrusion of the suspension into soft tissue.

34 Claims, 6 Drawing Sheets

INJECTABLE IMPLANT COMPOSITION HAVING IMPROVED INTRUDABILITY

TECHNICAL FIELD

The present invention is in the field of body-treating compositions. More particularly it relates to injectable implant compositions for soft tissue augmentation that comprises an aqueous suspension of a particulate biocompatible material and a biocompatible fluid lubricant.

BACKGROUND ART

The problem addressed by the present invention is how to nonsurgically implant a solid, often load-bearing, mass of biomaterial. The simple solution is to formulate the mass as an aqueous suspension of particles and inject it with a syringe or similar instrument into the tissue at the desired site. Depending on the material used and its concentration in the suspension, the injectability of the suspension may be less than adequate. Such inadequacy may manifest itself in terms of difficulties in extruding the suspension through a fine gauge needle and/or poor intrusion into the tissue. Common extrusion difficulties are excessive or irregular extrusion pressures and needle blockage. Poor intrusion is characterized by a tendency for the implant to intrude the tissue as a uniform front and form a solid bead rather than fingering into the tissue and forming a relatively dispersed, irregular-shaped mass.

Several prior U.S. patents or applications that are owned or licensed to the assignee of the present invention relate to injectable collagen-based implants for soft tissue augmentation.

U.S. Pat. No. 3,949,073 describes the use of a solution of atelopeptide collagen as an injectable implant for augmenting soft tissue. The solution is brought to physiological ionic strength and pH and injected with a small gauge needle. The collagen fibers reconstitute to produce a fibrous mass of collagen at the injection site. Since the solid content of the injected material is low and the reconstituted fibers are flexible and small, there are no extrusion or intrusion problems with this material.

U.S. Pat. No. 4,424,208 concerns an implant material comprised of a mixture of solid elastic particles of cross-linked collagen and reconstituted collagen fibers. While this material was injectable through medium gauge needles, its extrusion and intrusion properties were poor. The material did, however, exhibit improved persistence over the reconstituted uncross-linked material of U.S. Pat. No. 3,949,073 described above.

A cross-linked collagen implant material having improved extrusion properties over that described in U.S. Pat. No. 4,424,208 is claimed in commonly owned U.S. Pat. No. 4,582,640. This material was prepared under cross-linking conditions that produced predominantly intrafibrillar cross-links. In addition to lower viscosity, this "lightly cross-linked" collagen exhibits better persistence and resistance to proteolytic digestion than the previous materials. The extrudability of this material was improved further by mechanically shearing the reconstituted fibers before cross-linking. This mechanically shared, cross-linked collagen is the subject of commonly owned U.S. patent application Ser. No. 715,098, filed Mar. 22, 1985. Clinical testing of this improved material indicated that its intrudability was less than desired, particularly when it was injected intradermally for cosmetic purposes.

The present invention provides the technology for improving the injectability of implant suspensions of particulate biomaterials, such as the cross-linked collagen of the above-mentioned U.S. Patent Application, even further.

DISCLOSURE OF THE INVENTION

The present invention contemplates an injectable implant composition for soft tissue augmentation comprising an aqueous suspension amount of a biocompatible fluid lubricant to significantly improve the intrudability of the composition.

Expressed in alternative terms, the invention contemplates a method for improving the injectability of aqueous suspensions or particulate materials into soft tissue by incorporating such a lubricant into the suspension.

MODES FOR CARRYING OUT THE INVENTION

The two principal components of the injectable suspensions of the invention are: a biomaterial that provides the bulk of the implant and a biocompatible fluid that acts as a lubricant to improve the injectability of the biomaterial suspension. The biomaterial must meet several functional requirements in order to be useful as an implant for augmenting soft tissue. It must be nontoxic, well-tolerated by the body (i.e., produce no or tolerable levels of immune and inflammatory responses), and have mechanical properties that simulate those of soft tissue. It also must be relatively stable so that its properties do not significantly change in situ. Depending upon the body site at which the implant is placed, the material may also need to be relatively tough and elastic (i.e., capable of bearing loads without undergoing excessive or permanent deformation).

The biomaterial must be particulate in order for it to be implantable by injection. In this regard, the term "particle" and conjugates thereof are intended to include both fibrous and nonfibrous solid bodies. The biomaterial may be synthesized in the form of particles or be made originally in the form of a large solid body and then comminuted. The particle size of the biomaterial will depend upon the gauge of the needle that is to be used to inject it into the body. For precise placement of materials into tissues such as facial dermis, needles as fine as 27 gauge (200$\mu$ I.D.) or even 30 gauge (150$\mu$ I.D.) may be desirable. The maximum particle size that can be extruded through such needles will be a complex function of at least the following: particle maximum dimension, particle aspect ratio (length:width), particle rigidity, surface roughness of particles and related factors affecting particle-particle adhesion, the viscoelastic properties of the suspending fluid, and the rate of flow through the needle. Rigid spherical beads suspended in a Newtonian fluid represent the simplest case, while fibrous or branched particles in a viscoelastic fluid are likely to be much more complex. The size of rigid, generally spherical particles used in the invention will typically be in the range of 1 to 20 microns in diameter, whereas the size of deformable asymmetric particles will usually be 500–800 microns in length and less then 20 microns in width.

Examples of biomaterials that have been used or proposed for use in augmenting soft tissue are fibrillar cross-linked collagen, gelatin beads, and beads of natural or synthetic polymers such as polytetrafluoroethylene (TEFLON polymer), silicone rubber, and various hydrogel polymers such as polyacrylonitrile-polyacrylamide hydrogels. The fibrillar cross-linked collagen described in commonly owned U.S. Pat. No. 4,582,640 and U.S. patent application Ser. No. 715,098, the disclosures of which are incorporated herein by reference, is a preferred biomaterial for use in this invention.

The biomaterial is suspended in an aqueous medium at concentrations in the range of 1%–20% (W/V), more usually 3%–6%, with maximum concentrations depending on the particle characteristics. The aqueous medium will typically be buffered to physiological ionic strength and pH. It will also typically contain an effective amount of a local anesthetic (e.g., lidocaine) to ease the pain of the injection.

The second principal component of the injectable implant composition, the fluid lubricant, must also be tolerated by the body. While the invention is not dependent upon the mode of action of the lubricant in improving the injectability of the composition, it is believed that the lubricant acts by one or more of the following mechanisms:

(1) The hydrodynamic effect. Particles impact each other during passage from the syringe barrel into the needle. The impact time is sufficiently short that liquid cannot escape from between the particle surfaces, and the pressure in the liquid layer rises. If the pressure rise is great enough, the colliding particles will not make contact. This effect is enhanced by higher impact velocities and higher lubricant viscosity.

(2) The boundary layer effect. This mechanism is especially relevant to sliding contact of surfaces. Lubricant molecules bind to the particle surface only a few molecular layers thick, and particle-particle contact is largely prevented by this layer. The coefficient of friction between such opposing surfaces is greatly reduced. The ability of the lubricant molecule to form a surface layer on the particle with strong lateral adhesion between lubricant molecules is crucial in this mechanism of action.

(3) Elastic recoil. If the lubricant is an elastic fluid it can resist deformation as it is compressed between colliding particles. A shear thinning viscoelastic fluid may be especially suitable, since under low shear at the particle surface (boundary layer) the lubricant behaves as a viscous, elastic fluid. Far from the particle surface, in regions of high shear, such fluids are dramatically less viscous and offer low resistance to bulk flow.

The above three mechanisms facilitate flow by preventing particle-particle contact, which is a major factor in particle "bridging", or agglomeration, to plug the extrusion orifice. An additional factor to be considered is:

(4) Disruption of fiber structure by lubricants. Some fibers are present in agglomerates or clumps. If such clumps are maintained by non-covalent bonds, they may be disrupted in the presence of salts, especially chaotropic agents, and by detergents. If the average fiber dimensions or clump dimensions are reduced, extrusion should be facilitated.

The lubricant should be capable of being sterilized by conventional techniques (e.g. autoclaving, filtering, irradiation) used in the manufacture of pharmaceuticals and medical devices. It is preferably nonfibrillar and soluble in the aqueous suspending medium. Examples of materials that may be used as lubricants in the invention composition are hyaluronic acid, dextran sulfate, dextran, succinylated noncrosslinked collagen, methylated noncross-linked collagen, glycogen, glycerol, dextrose, maltose, triglycerides of fatty acids such as corn oil, soybean oil, and sesame oil, and egg yolk phospholipid.

The minimum amount of lubricant in the biomaterial suspension is that amount which provides a significant improvement in the intrudability of the biomaterial into body tissue. In this regard acceptable intrudability is characterized by homogeneous flow of the the composition into the tissue with fingering and without tearing or otherwise damaging the tissue. As used herein the term "fingering" has essentially the same meaning as this term has in the context of geology and denotes irregular movement into the tissue interstices rather than intrusion along a uniform front. In contrast, unacceptable intrudability is characterized by failure of the compositon to intrude as a homogeneous mass with retention of the particulate biomaterial and expression of the suspending medium through the tissue. In this case the composition does not finger into the tissue but forms a bead at the site of injection. Such beading is particularly undesirable when the composition is being injected for cosmetic purposes at normally visible body sites (e.g., the face) in that the resulting bead may be unsightly. Poor intrudability is often accompanied by poor extrudability from the needle—that is, the force of extrusion is extremely irregular (commonly referred to as "spiking") or the needle becomes blocked by the composition. Spiking or blockage may cause the composition to ooze from the syringe rather than be injected into the tissue.

In quantitative terms the amount of lubricant that is required to be included in the composition in order to achieve significant intrusion enhancement will vary depending on the quality of the lubricant and, perhaps, the particulate biomaterial involved.

The weight fraction of lubricant component (weight to total suspension volume) will usually range from about 0.01% to 40%, with the optimum concentration depending on the particular lubricant. By way of example, when the biomaterial is the sheared lightly cross-linked collagen described above and the lubricant is uncross-linked methylated or succinylated collagen, the weight fraction of lubricant will normally be in the range of 0.1% to 3%. If hyaluronic acid is used in place of uncross-linked collagen, the weight fraction will usually be in the range of 0.3% to 0.5%. If maltose is the lubricant, a weight fraction as high as 40% may be used. The operable amounts of other lubricants may be estimated by in vitro intrusion tests using a bed of particulate material such as hydroxylapatite or silicon carbide to simulate living tissue - such as the dermis.

The particulate biomaterial and the lubricant are preferably combined by adding a 1% to 10% (W/V) biocompatible nonaqueous or aqueous solution or suspension, as the case may be, of the lubricant to an aqueous suspension of the particulate biomaterial. The biomaterial and lubricant are combined in a manner that provides a homogeneous mixture. For instance, the two components may be mixed homogeneously by repeated passages through pumps or by repeated transfer from one syringe to another through a small diameter interconnecting channel (200–1000$\mu$ inside diameter).

The injectable implant compositions of this invention may be injected intradermally or subcutaneously into humans or other mammals to augment soft tissue, to correct congenital anomalies, acquired defects of cosmetic defects. They may also be injected into internal tissues such as the tissue defining sphincters to augment such tissue. The specific uses of collagenous biomaterials for tissue augmentation are detailed in the above referenced commonly owned patents and applications.

The following examples illustrate embodiments of the invention and their injection properties. These examples are not intended to limit the invention in any manner.

EXAMPLE 1

This example illustrates injectable suspensions of cross-linked collagen in which hyaluronic acid is used as a lubricant to enhance injectability.

Formulation

A 35 mg/ml (3.5% W/V) aqueous suspension of particulate ($40 \times 2\mu$ to $800 \times 30\mu$) glutaraldehyde cross-linked atelopeptide bovine collagen in 0.02 M sodium phosphate and 0.13 M sodium chloride, pH 7.2 (Buffer A) was prepared as described in the examples of said U.S. patent application Ser. No. 715,098. A 24 mg/ml solution of hyaluronic acid (mol. wt. approximately $2.3 \times 10^6$) in physiological saline was prepared. A 0.9 ml portion of the suspension was blended with 0.1 ml of the hyaluronic acid solution by pumping the mixture between two syringes coupled with a #12 gauge connector.

Intrusion Tests

Figure 1A:
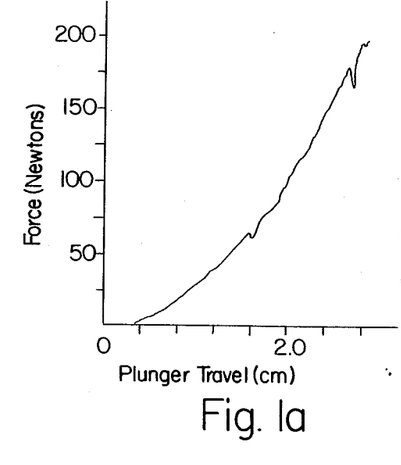
FIGS. 1–5 are graphs of the results of the intrusion/extrusion tests described in Examples 1–4, infra.
Figure 1B:
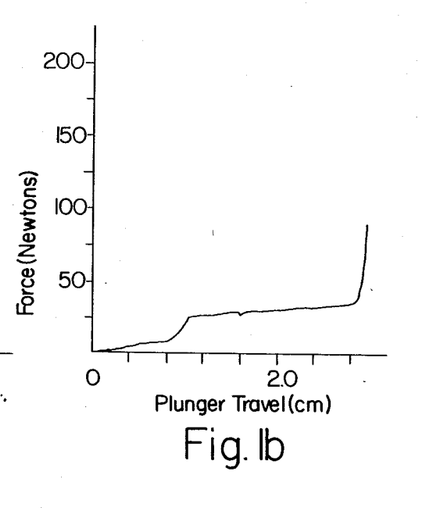

The barrels of ¼ cc syringes (0.65 cm diameter) fitted with #27 gauge needles ($200\mu$ inside diameter, 1.26 cm length) were loaded with approximately 0.5 cm³ of particulate silicon carbide (#60 Grit, mean particle diameter approximately 450 microns) and 1 ml of the blend was loaded on top of the silicon carbide beds. (Hydroxylapatite, mean particle diameter 700 microns, may be used in place of silicon carbide). The blend was plunged through the bed at a plunger speed of 2 cm/min (vol. flow rate=0.66 cm³/min) with the force exerted on the plunger being monitored with an Instron Model 4202 tensile testing apparatus. For comparison purposes, unlubricated suspension was also tested. FIGS. 1(a) (unlubricated) and 1(b) (lubricated) are plots of the results of these intrusion tests with force (in Newtons) plotted relative to plunger travel (in cm).

In the in vitro intrusion plots shown in FIG. 1, a plateau in the plot indicates capillary flow of the suspension through the bed. The absence of a plateau indicates plugging of the channels in the bed causing the force required to push the suspension through the bed to increase. The pattern shown in FIG. 1(a) indicates that the glutaraldehyde cross-linked collagen alone plugged the bed and produces some spiking. This caused free buffer to be expressed through the bed. In contrast, the suspension containing hyaluronic acid exhibited free intrusion at 25 to 35 Newtons with the homogeneous blend being expressed through the bed.

EXAMPLE 2

This example reports the results of testing other materials as lubricants for suspensions of the cross-linked collagen of Example 1.

Formulations Studied

A series of suspensions of the glutaraldehyde cross-linked collagen of Example 1 containing the lubricants listed in Table 1 below were prepared. All blends contained Buffer A as the aqueous component. Intrusion tests were carried out as in Example 1. The results of some of these tests are plotted in FIGS. 2 and 3. Other results are included in Table 1, with plus (+) indicating acceptable intrusion and minus (−) indicating unacceptable intrusion.

TABLE 1

Figure 2A:
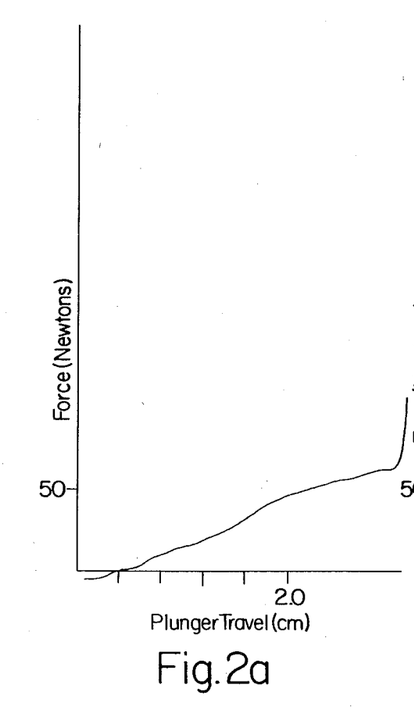
Figure 2B:
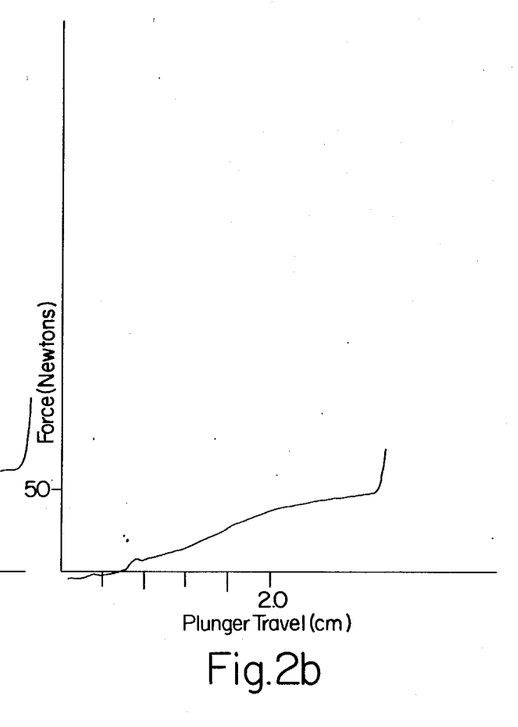
Figure 3:
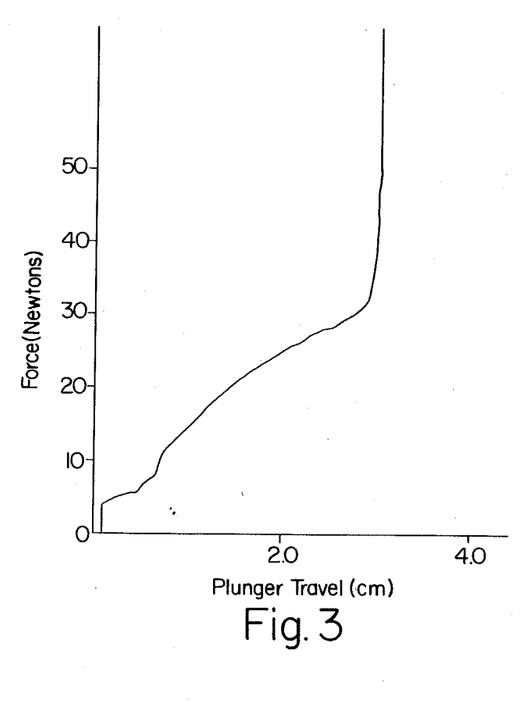

| Sample | Intrusion Observed (+ or −) | Cross-linked Collagen Weight Fraction (%) | Weight Fraction of Lubricant (%) | Nature of Lubricant |
|---|---|---|---|---|
| 1 | + | 3.2 | 0.3 | methylated collagen (FIG. 2(a)) |
| 2 | + | 3.2 | 0.3 | succinylated collagen (FIG. 2(b)) |
| 3 | − | 2.1 | 0.1 | dextran sulfate 8000 mol. wt. |
| 4 | + | 2.1 | 0.01 | dextran sulfate 500,000 mol. wt. |
| 5 | + | 2.5 | 30 | dextran 10,000 mol. wt. |
| 6 | − | 2.1 | 0.1 | dextran 10,000 mol. wt. |
| 7 | − | 2.1 | 0.01 | dextran 500,000 mol. wt. |
| 8 | + (high force) | 2.5 | 30 | heparin 8000 mol. wt. |
| 9 | − | 2.5 | 30 | polyethylene glycol 1540 mol. wt. |
| 10 | + | 3.0 | 15 | rabbit liver glycogen (up to 80 million mol. wt.) (FIG. 3) |

In terms of intrusion behavior, there were at least three classes of results: (1) Methylated collagen (bearing a positive charge), succinylated collagen (negative charge), and high molecular weight dextran sulfate (negative charge) facilitated flow of particulate cross-linked collagen, and very low levels (0.01% to 1% W/V) of lubricant were required; (2) There was a second class of uncharged polymers, such as dextran (Sample 5), heparin, and glycogen which facilitated flow, but at high concentration; and (3) The remaining polymeric samples are all uncharged and did not facilitate flow into porous beds.

Samples 3, 6, and 7 would probably facilitate flow if used at higher (10%–40%) weight fractions. Polyethylene glycol is not a lubricant at high weight fraction; this may be due to the fact that it promotes precipitation of proteins. Partially precipitated cross-linked collagen would be expected to block channels in the bed.

Although the detailed mechanism in each case above is not defined, it appears that high molecular weight charged polymers are effective lubricants for particulate collagen. Presumably charged polymers can bind to the surface of cross-linked collagen particles better than non-charged polymers (boundary layer effect). Furthermore, charged polymers will carry a bound water layer, which can be elastically displaced under collision stress, possibly leading to more elastic recoil between colliding particles (elastic effect). In principle, these materials appear the most suitable for biomedical applications because of the low concentration levels required.

The second class of materials, high molecular weight neutral polymers (Samples 5–7, and 10) presumably function as lubricants becuase of their viscous properties, which are only manifested at higher weight fractions (hydrodynamic effect).

EXAMPLE 3

This example illustrates the lubricating effect of hyaluronic acid on flow of suspensions of polymeric beads or glass beads. The glass beads may be considered as model particulates for a wide variety of biomaterials.

Formulation

Suspensions of glass beads (3–10$\mu$ and 10–30$\mu$ diameter) in 0.1% xanthan solution were prepared by adding 20.0 mg of glass beads to 10.0 ml of xanthan solution. Solutions of 3.0 mg/ml hyaluronic acid (mol. wt. $2.3 \times 10^6$) were then added to each suspension (90/10 V/V) as a lubricant.

Extrusion Tests

The samples were subjected to extrusion from syringes (0.65 cm inside diameter, volume flow rate 0.66 cm$^3$/min) in which there was no porous bed and the syringes were fitted with 30 gauge needles (150$\mu$ I.D., 1.25 cm length). This is equivalent to extrusion from a reservoir through a capillary die. Plots of the test results are shown in FIGS. 4(a), (b) and (c).

Figure 4A:
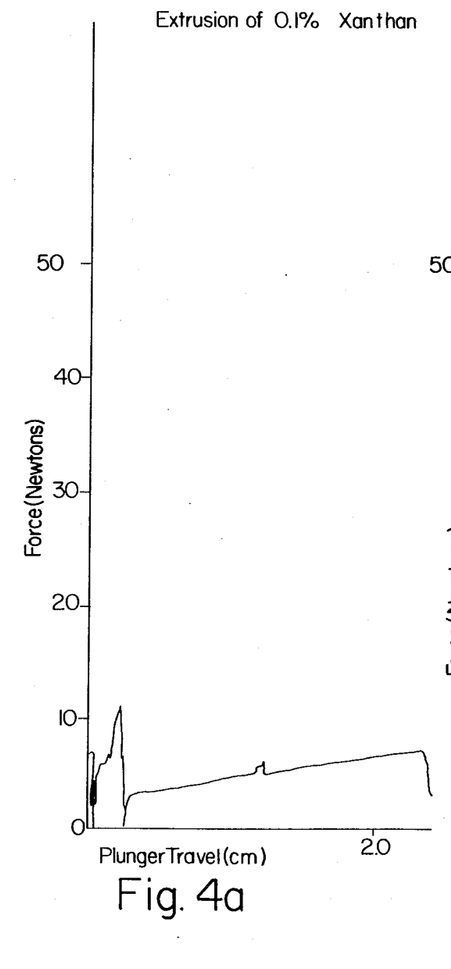
Figure 4B:
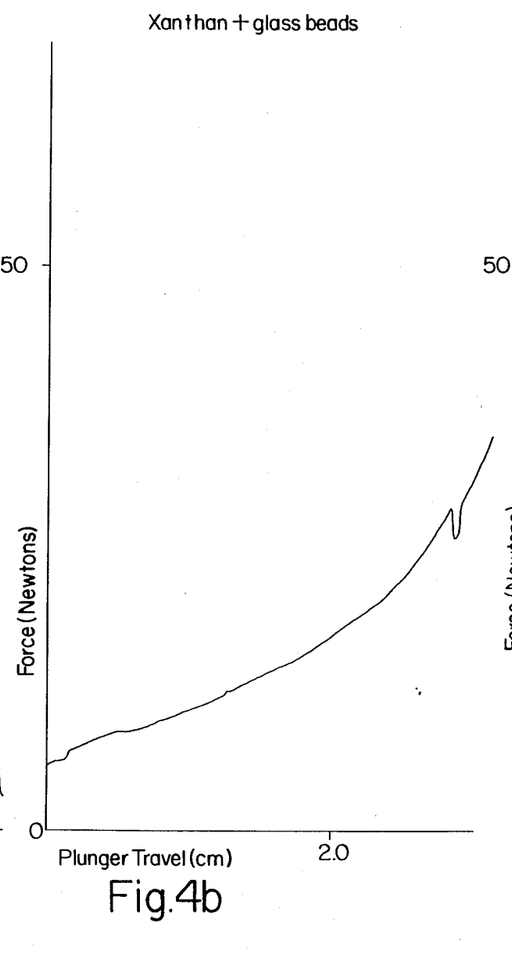
Figure 4C:
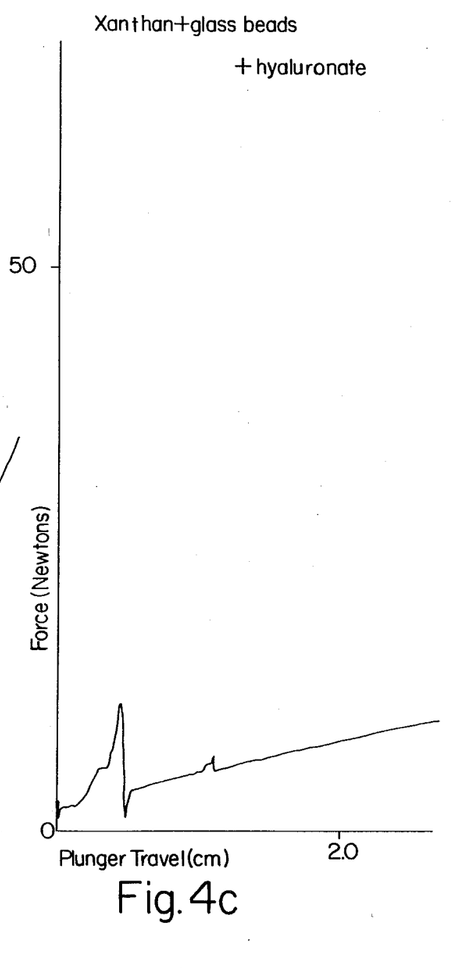
Figure 5A:
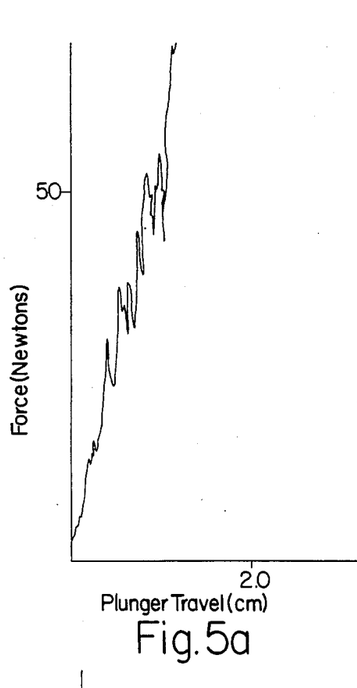
Figure 5B:
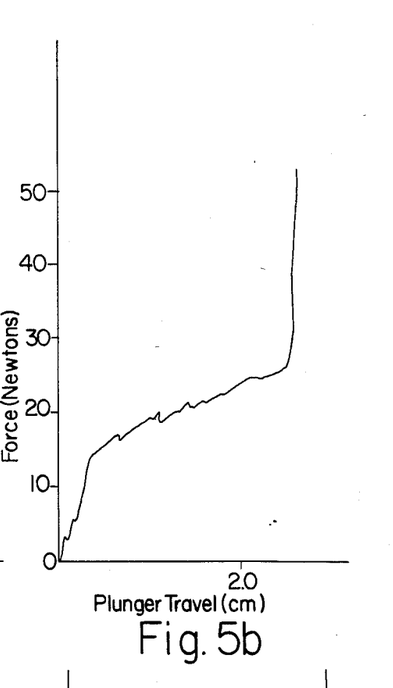
Figure 5C:
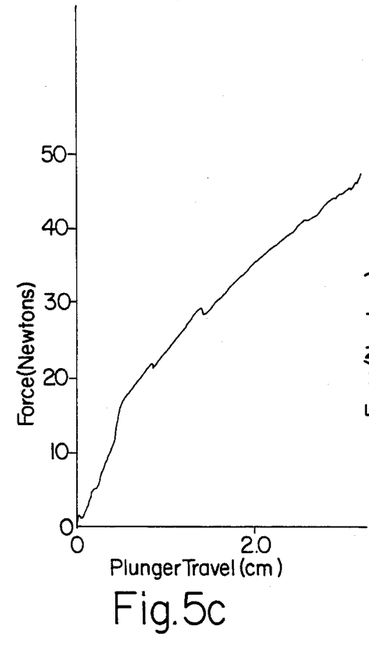
Figure 5D:
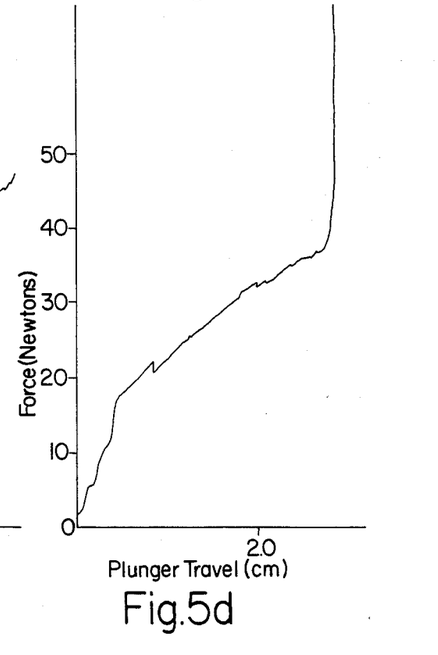
Figure 5E:
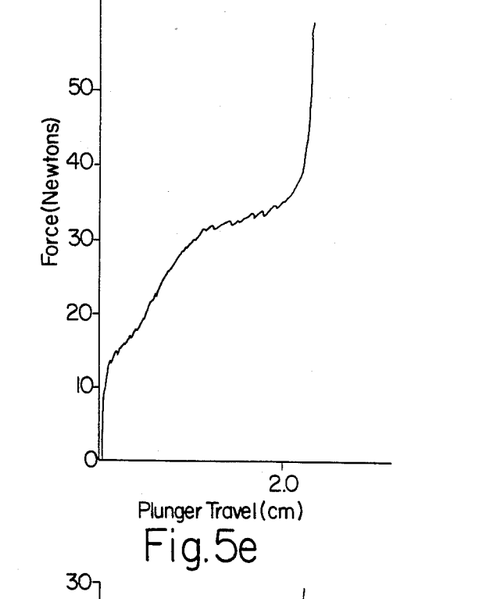
Figure 5F:
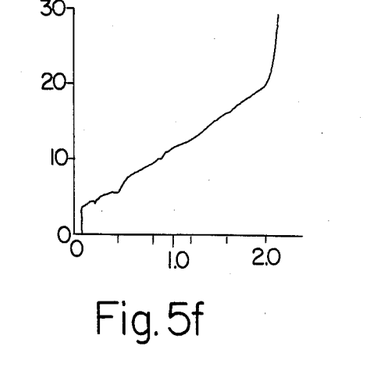

As shown in FIG. 4(a), xanthan solution extrudes freely through a 30 gauge needle at 4 to 8 Newtons. However, suspensions of glass beads in xanthan solution exhibit numerous spikes in the extrusion plot (for the 3–10$\mu$ diameter glass bead suspension) or cause a partial blockage of the 30 gauge needle (10–30$\mu$ diameter glass bead suspension) (FIG. 4(b)). In contrast, when these suspensions are lubricated with hyaluronic acid solution, they extrude freely through a 30 gauge needle at 4–10 Newtons (FIG. 4(c)). Hyaluronic acid can thus facilitate flow of two completely different particulate materials.

EXAMPLE 4

The following low molecular weight materials were tested as lubricants for the cross-linked collagen of Example 1: glycerol, maltose, dextrose, and corn oil. Plots of the results of these tests as shown in FIG. 5(a)-(f) as follows (percentages are W/V):

| Plot | Blend |
|---|---|
| 5(a) | None (cross-linked collagen in Buffer A) |
| 5(b) | 3.2% cross-linked collagen, 10% glycerol |
| 5(c) | 2.5% cross-linked collagen, 30% maltose |
| 5(d) | 2.1% cross-linked collagen, 40% maltose |
| 5(e) | 3.0% cross-linked collagen, 15% corn oil |
| 5(f) | 2.1% cross-linked collagen, 40% dextrose |

As shown in these Figures relatively low intrusion forces were observed when these materials were used in high weight fraction (10%–40%). Because of their low cost and relative biocompatibility, these materials may also be suitable lubricants. These materials will exhibit a substantial osmotic effect in vivo and care should be taken in their use.

Table 2 summarizes the lubricants of the Examples and their possible mechanism of lubrication.

TABLE 2
PROPERTIES OF LUBRICANTS FOR PARTICULATE, INJECTABLE BIOMATERIALS

| Physical Property Class | Possible Mechanism of Lubrication |
|---|---|
| 1. High molecular weight charged polymers<br>hyaluronic acid<br>dextran sulfate<br>succinylated collagen<br>methylated collagen<br>heparin | boundary layer,<br>elastic,<br>hydrodynamic |
| 2. High molecular weight neutral polymers<br>glycogen<br>dextran | hydrodynamic<br>(poss. boundary layer or disruption) |
| 3. Low molecular weight neutral molecules<br>fatty acid esters of glycerol (corn oil)<br>glycerol<br>maltose<br>dextrose | hydrodynamic<br>or disruption |

Modifications of the above described modes for carrying out the invention that are obvious to those of skill in the biochemical, medical, and/or surgical arts are intended to be within the scope of the following claims.

We claim:

1. An injectable implant composition for soft tissue augmentation comprising an aqueous suspension of a particulate biomaterial containing a sufficient amount of a biocompatible fluid lubricant to significantly improve the intrudability of the composition, wherein said particles of biomaterial are fibrils or beads comprising natural or synthetic polymers, and wherein said fluid lubricant comprises a non-fibrillar high molecular weight charged polymer, a high molecular weight neutral polymer, or a low molecular weight neutral molecule.

2. The composition of claim 1 wherein the particulate biomaterial is fibrillar cross-linked collagen, or beads of a synthetic or natural polymer.

3. The composition of claim 1 wherein the particles of biomaterial are (a) generally spherical in shape and have diameters in the range of about 1 to 30 microns or (b) are 500–800 microns in length and less than 30 microns in width.

4. The composition of claim 1 wherein the concentration of particulate biomaterial in the suspension is in the range of 1% to 20% W/V.

5. The composition of claim 1 wherein the concentration of particulate biomaterial in the suspension is in the range of 3% to 6% W/V.

6. The composition of claim 1 wherein the concentration of said lubricant in the suspension is about 0.01% to 40% W/V.

7. The composition of claim 1 wherein the lubricant is a charged polymer.

8. The composition of claim 7 wherein the charged polymer is methylated collagen, succinylated collagen, or dextran sulfate.

9. The composition of claim 1 wherein the lubricant is an uncharged polymer selected from the group consisting of dextran, heparin, and glycogen, and the concentration of lubricant in the suspension is 10% to 40% W/V.

10. The composition of claim 1 wherein the lubricant is neutral, has a low molecular weight, and is present in the suspension at 10% to 40% W/V.

11. The composition of claim 10 wherein the lubricant is maltose, dextrose, a triglyceride of a fatty acid, egg yold phospholipid, or glycerol.

12. The composition of claim 1 wherein the lubricant is hyaluronic acid.

13. The composition of claim 1 wherein the lubricant is soluble in the suspending medium.

14. The composition of claim 8 wherein the biomaterial is cross-linked collagen and the concentration of biomaterial in the suspension is 3% to 6% W/V.

15. The composition of claim 9 wherein the biomaterial is cross-linked collagen and the concentration of biomaterial in the suspension is 3% to 6% W/V.

16. The composition of claim 11 wherein the biomaterial is cross-linked collagen and the concentration of biomaterial in the suspension is 3% to 6% W/V.

17. The composition of claim 12 wherein the biomaterial is cross-linked collagen and the concentration of biomaterial in the suspension is 3% to 6% W/V.

18. A method of improving the intrudability of a particulate biomaterial into soft tissue comprising incorporating a sufficient amount of a biocompatible fluid lubricant in the suspension to enhance the intrudability of the suspension into the tissue, wherein said particles of biomaterial are fibrils or beads comprising natural or synthetic polymers, and wherein said fluid lubricant comprises a non-fibrillar high molecular weight charged polymer, a high molecular weight neutral polymer, or a low molecular weight neutral molecule.

19. The method of claim 18 wherein the concentration of said lubricant in the suspension is about 0.01% to 40% W/V.

20. The method of claim 18 wherein the lubricant is a charged polymer.

21. The method of claim 20 wherein the charged polymeric methylated collagen, succinylated collagen, or dextran sulfate.

22. The method of claim 18 wherein the lubricant is an uncharged polymer selected from the group consisting of dextran, heparin, and glycogen and the concentration of lubricant in the suspension is 10% to 40% W/V.

23. The method of claim 18 wherein the lubricant is neutral, has a low molecular weight and is present in the suspension at 10% to 40% W/V.

24. The method of claim 23 wherein the lubricant is maltose, dextrose, a triglyceride of a fatty acid, egg yolk phospholipid, or glycerol.

25. The method of claim 18 wherein the lubricant is hyaluronic acid.

26. A method for augmenting soft tissue in a living mammal comprising injecting the composition of claim 1 into the mammal at the augmentation site.

27. A method for augmenting soft tissue in a living mammal comprising injecting the composition of claim 8 into the mammal at the augmentation site.

28. A method for augmenting soft tissue in a living mammal comprising injecting the composition of claim 9 into the mammal at the augmentation site.

29. A method for augmenting soft tissue in a living mammal comprising injecting the composition of claim 11 into the mammal at the augmentation site.

30. A method for augmenting soft tissue in a living mammal comprising injecting the composition of claim 12 into the mammal at the augmentation site.

31. The composition of claim 1 wherein said biomaterial is selected from fibrillar crosslinked collagen, gelatin beads, polytetrafluoroethylene beads, silicone rubber beads, hydrogel beads, silicon carbide beads, and glass beads.

32. The composition of claim 1 wherein said fluid lubricant is selected from hyaluronic acid, dextran sulfate, dextran, succinylated non-crosslinked collagen, methylated non-cross-linked collagen, glycogen, glycerol, dextrose, maltose, triglycerides of fatty acids, egg yolk phospholipids, and heparin.

33. The method of claim 18 wherein said biomaterial is selected from fibrillar cross-linked collagen, gelatin beads, polytetrafluoroethylene beads, silicone rubber beads, hydrogel beads, silicon carbide beads, and glass beads.

34. The method of claim 18 wherein said fluid lubricant is selected from hyaluronic acid, dextran sulfate, dextran, succinylated non-cross-linked collagen, methylated non-cross-linked collagen, glycogen, glycerol, dextrose, maltose, triglycerides of fatty acids, egg yolk phospholipids, and heparin.

* * * * *

UNITED STATES PATENT AND TRADEMARK OFFICE
CERTIFICATE OF CORRECTION

PATENT NO. : 4,803,075

DATED : Feb. 7, 1989

INVENTOR(S) : Wallace et al.

It is certified that error appears in the above-identified patent and that said Letters Patent is hereby corrected as shown below:

Column 9, line 39:

In claim 18, line 1, after "intrudability of"

insert -- an aqueous suspension of --.

Signed and Sealed this

Fourth Day of February, 1992

*Attest:*

HARRY F. MANBECK, JR.

*Attesting Officer*  *Commissioner of Patents and Trademarks*